March 6, 1945. T. J. MORRIS Plant Pat. 652
ROSE PLANT
Filed June 22, 1944
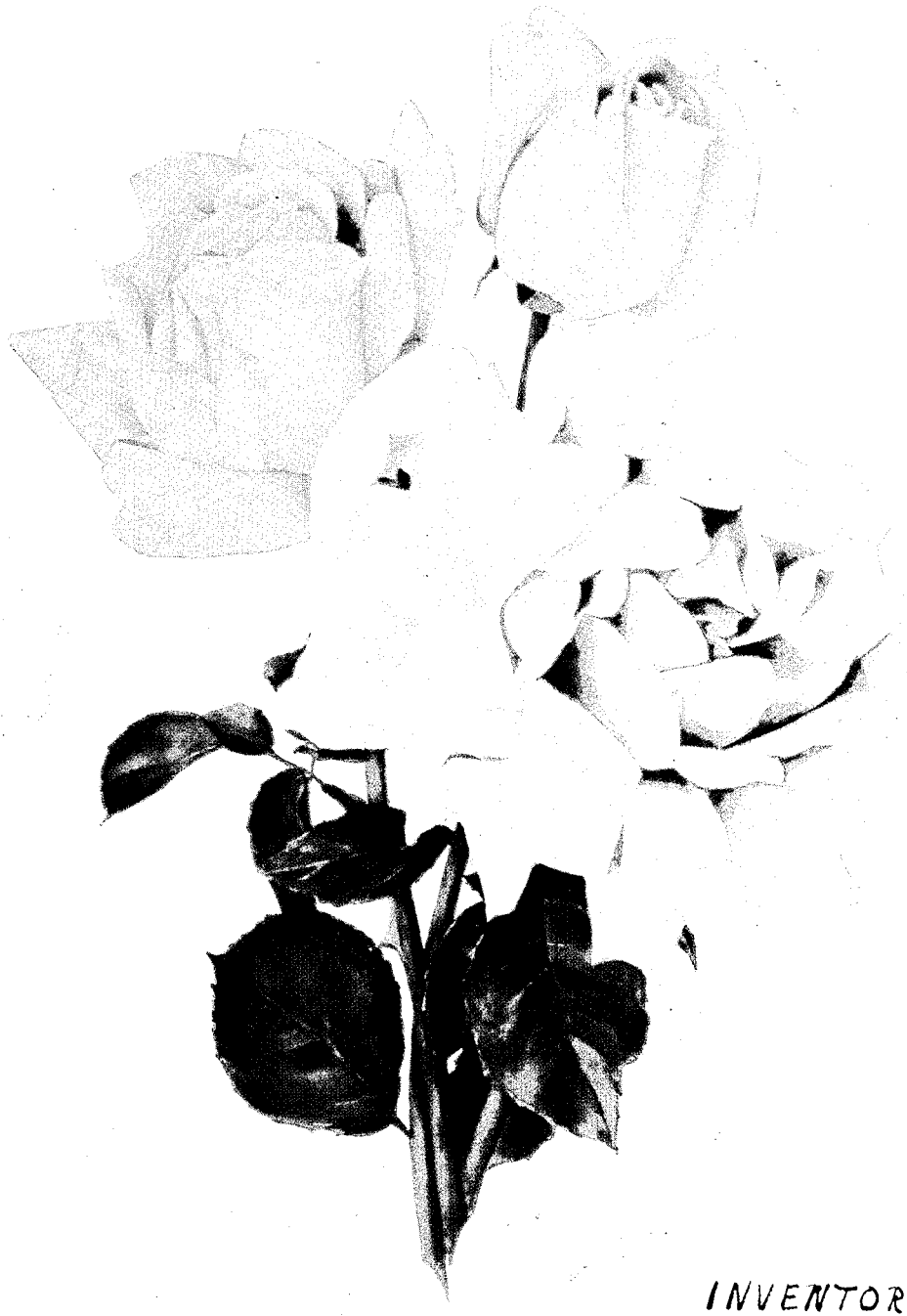
INVENTOR
Theodore J. Morris
By Orville M. Kile
Plant Pat. Agt.

Patented Mar. 6, 1945

Plant Pat. 652

UNITED STATES PATENT OFFICE

652

ROSE PLANT

Theodore J. Morris, Van Nuys, Calif., assignor to Germain Seed and Plant Company, Los Angeles, Calif., a corporation of California Application June 22, 1944, Serial No. 541,585

1 Claim. (Cl. 47—61)

My present invention is an improvement of hybrid tea roses in the class producing red flowers, and is the result of definite breeding efforts made by me. The new variety resulted from a cross between Sœur Therese and Signora, the former being the seed parent and the latter the pollen parent.

The most remarkable feature of this new rose variety is the giant size of the flowers since they frequently attain a size of 6 to 7 inches in diameter and even larger at times. Since the plant blooms profusely and continuously a great many of these large flowers are produced, averaging about 40 blooms per season per plant. These remarkable blooming habits coupled with vigorous growth, disease resistance, and colorful substantial petals of the flower make a very outstanding rose variety.

The accompanying illustration which is a part of this specification shows three specimens of the bloom of this variety in various stages of opening, together with some of the stem and foliage. These are in as nearly true colors as the artist could portray them although it must be understood that there may be variations because of circumstances of growth. The original paintings show the flowers slightly reduced in size.

Following is a detailed description of the plant and flower of this new rose variety. Color plate references indicate the "Horticultural Colour Chart" issued jointly by the British Colour Council and the Royal Horticultural Society of England.

*The plant*

Form: Bush.

Growth: Very vigorous; branching.

Blooming habit: Blooms profusely and continuously, producing about 40 blooms per season.

Foliage: Five leaflets.

*Size.*—Large, terminal leaflet measures 2¾ inches long by 2 inches at its widest part. Bottom leaflets measure 1¾ by 1⅜ inches.

*Quantity.*—Normal.

*Color.*—New foliage dark green on upper side, bronze green on under side. Old foliage dark green on upper side, normal green on under side.

*Shape.*—Oval.

*Edge.*—Serrated.

*Serrations.*—Single; small.

*Ribs and veins.*—Ordinary.

*Rachis.*—Color green; under side with prickles.

*Stipules.*—Medium size; smooth.

*Texture.*—Smooth and substantial.

*Disease resistance.*—Excellent.

Stems: Very strong.

Wood: New wood bronzy with smooth bark. Old wood green with smooth bark.

Thorns:

*Quantity.*—On main stalk and on laterals, ordinary quantity.

*Form.*—Narrow base, medium length, hooked downward.

*Color.*—Red when young; dark brown when old.

*Position.*—Irregular.

*Prickles.*—None on main stalks or laterals.

*Short needles.*—None on main stalks or on laterals.

*The flower*

Bud:

*Size.*—Very large; length 2 inches or more.

*Shape.*—Urn shaped.

*Color.*—Tyrian Rose (Plate #24–1) inside of petals. Neyron Rose (Plate 623–1) reverse of petals.

*Calyx.*—Funnel shaped; broad; smooth; apple odor when rubbed.

*Peduncle.*—Length—medium. Aspect—smooth. Color—bronzy. Strength—stiff and heavy.

*Opening.*—Bud opens well; not affected by adverse conditions.

Bloom:

*Size.*—Exceedingly large. When expanded the open flower attains a size of six to seven inches across when grown under favorable conditions.

*Borne.*—Singly.

*Form.*—Globular or high centered at first, opening into informal or dahlia form with petals turned backward but not tightly curled.

*Permanence.*—Never becomes flat.

*Petalage.*—Very double. Usual number of petals under normal conditions is 50 to 60.

*Color.*—Center of flower, Turkey Red (Plate 721/2). Outer petals, Tyrian Rose (Plate 24/1). Base of petals, Straw Yellow (Plate 604). Inside of petals, Cardinal Red. Reverse of petals, Tyrian Rose (Plate 24/2), lightened by copper. General tonality from a distance, Neyron Rose.

*Variegation.*—None.

*Discoloration.*—General tonality at end of first day, Turkey Red. General tonality second day, Cardinal Red. General tonality third day, Tyrian Rose.

Petals:

*Texture.*—Thick; not affected by hot or cold weather.

*Appearance.*—Satiny both inside and outside.

*Form.*—Oval.

*Arrangement.*—Imbricated in the opening rose but irregular or informal in the fully open rose.

*Petaloids in center.*—Few.

*Persistence.*—Drop off cleanly.

*Fragrance.*—Slight; briar odor.

*Lastingness.*—Flowers keep well both on bush and when cut.

Genital organs:

*Stamens.*—*Anthers*—many and medium in size; Yellow in color and arranged regularly around styles. *Filaments*—medium length; Yellow.

*Pistils.*—*Styles*—bunched, even and medium in length. *Stigmas*—white.

*Pollen.*—Gold Yellow.

*Ovaries.*—Some protruding from calyx.

Fruit: Variety is sterile with its own pollen.

*Form.*—Funnel shaped.

*Aspect.*—Smooth.

*Color at maturity.*—Russet brown.

*Sepals.*—Permanent and straight.

Having thus disclosed my invention, I claim:

The new and distinct variety of hybrid tea rose plant substantially as shown and described, characterized particularly by its health and vigor of growth, its strength of stems; and its prolific production of exceedingly large flowers of distinctive red to copper coloring as indicated.

THEODORE J. MORRIS.